United States Patent [19]

Grimes

[11] Patent Number: 4,795,473

[45] Date of Patent: Jan. 3, 1989

[54] EXTRAMEDULLARY FEMORAL HEAD-NECK PROSTHESIS AND METHOD OF IMPLANTING SAME

[76] Inventor: James B. Grimes, 15301 Vista Grande Dr., Bakersfield, Calif. 93306

[21] Appl. No.: 1,827

[22] Filed: Jan. 9, 1987

[51] Int. Cl.⁴ .......................... A61F 2/36; A61F 5/09
[52] U.S. Cl. .................................. 623/23; 128/92 YL; 128/92 YK
[58] Field of Search ........... 128/92 Y, 92 YX, 92 YT, 128/92 YP, 92 YM; 623/16, 17, 18, 19, 20, 21, 22, 23

[56] References Cited

U.S. PATENT DOCUMENTS 4,129,903  12/1978  Huggler .............................. 623/23

FOREIGN PATENT DOCUMENTS

86/03962  7/1986  PCT Int'l Appl. .................... 623/23
2166359  5/1986  United Kingdom .................. 623/23

*Primary Examiner*—Richard J. Apley
*Assistant Examiner*—David Isabella
*Attorney, Agent, or Firm*—Senniger, Powers, Leavitt and Roedel

[57] ABSTRACT

An extramedullary femoral head-neck prosthesis for implantation in a femur, the latter having a shaft and a neck at the upper end of the shaft at the medial side of the femur. The prosthesis comprises a sideplate and screws for securing the sideplate to the lateral side of the femoral shaft. A barrel extends obliquely upwardly from the sideplate and has an open upper end. The barrel is adapted to be inserted in a bore extending obliquely upwardly through the femoral shaft from the lateral side of the shaft to the femoral neck. The prosthesis also includes a ball assembly comprising a ball stem adapted to be inserted coaxially into the barrel through the open upper end of the barrel and to be slideably received therein, a neck at the upper end of the stem adapted for face-to-face engagement with the femoral neck, and a ball on the neck. The ball stem is sized for a relatively close clearance fit in the barrel. The ball stem is retained and held against upward movement in the barrel so that the neck of the ball assembly presses against and compresses the femoral neck. A method of implanting such a prosthesis is also disclosed.

9 Claims, 4 Drawing Sheets

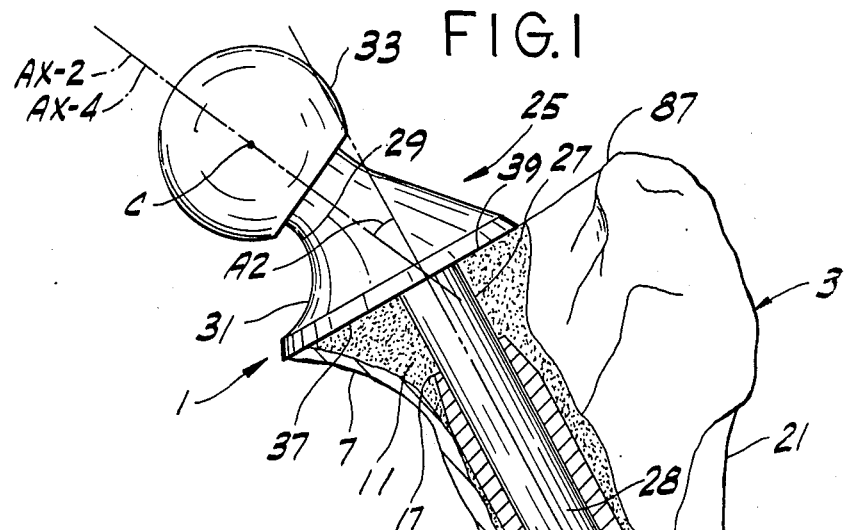
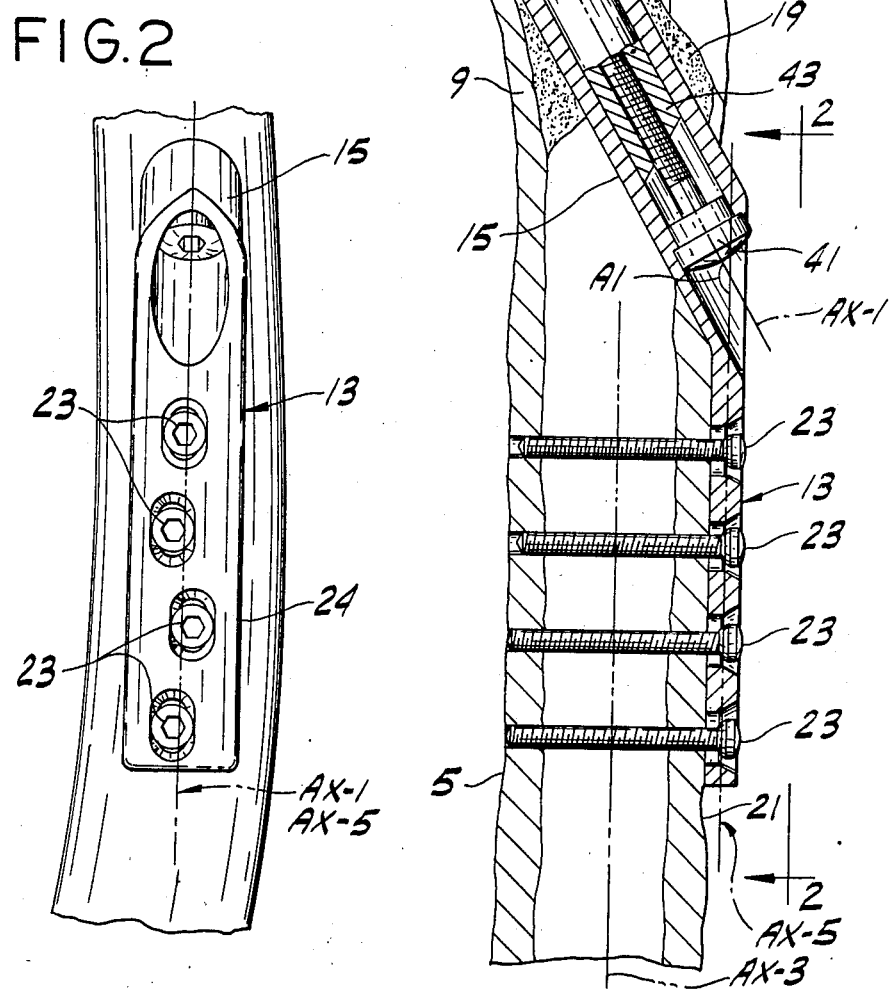

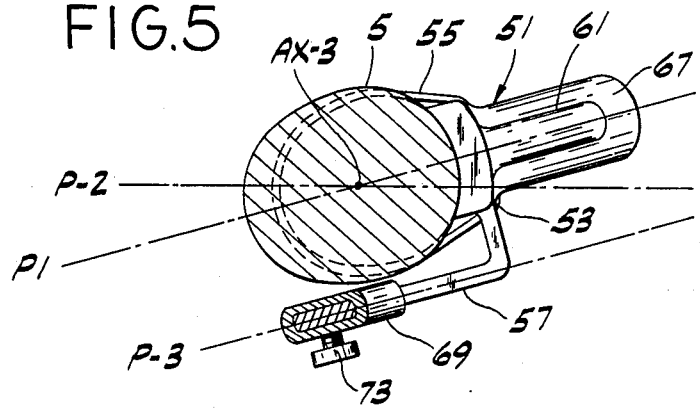
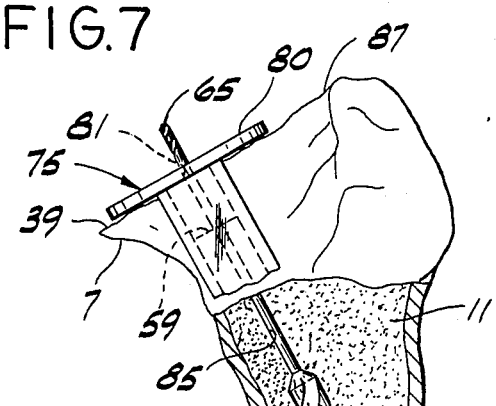
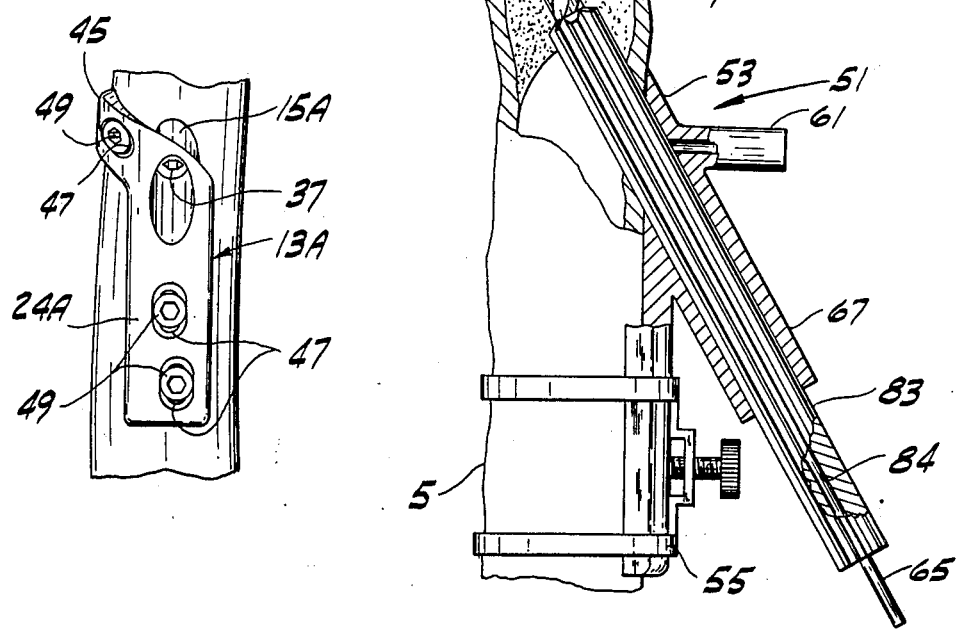

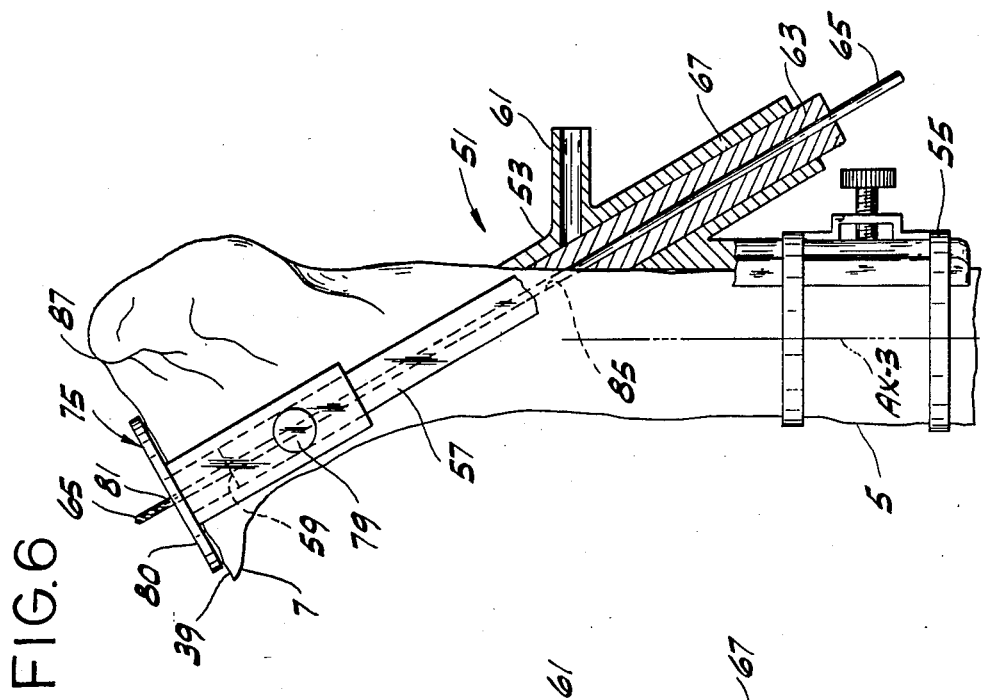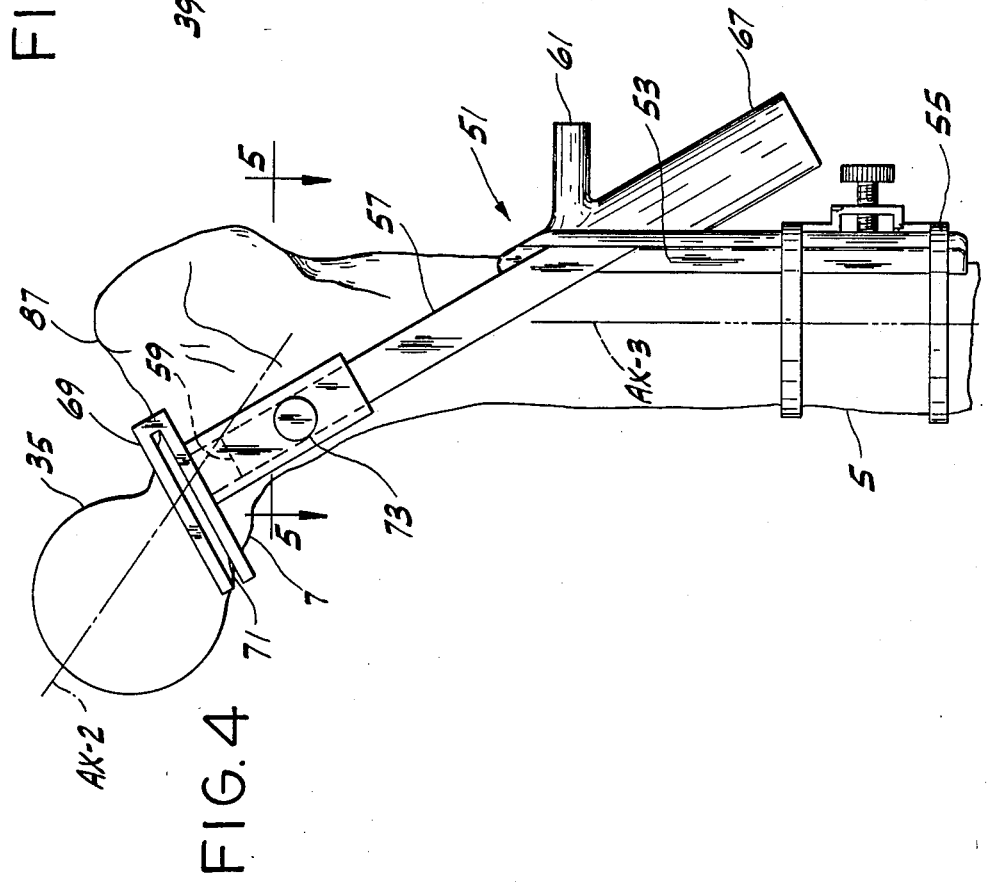

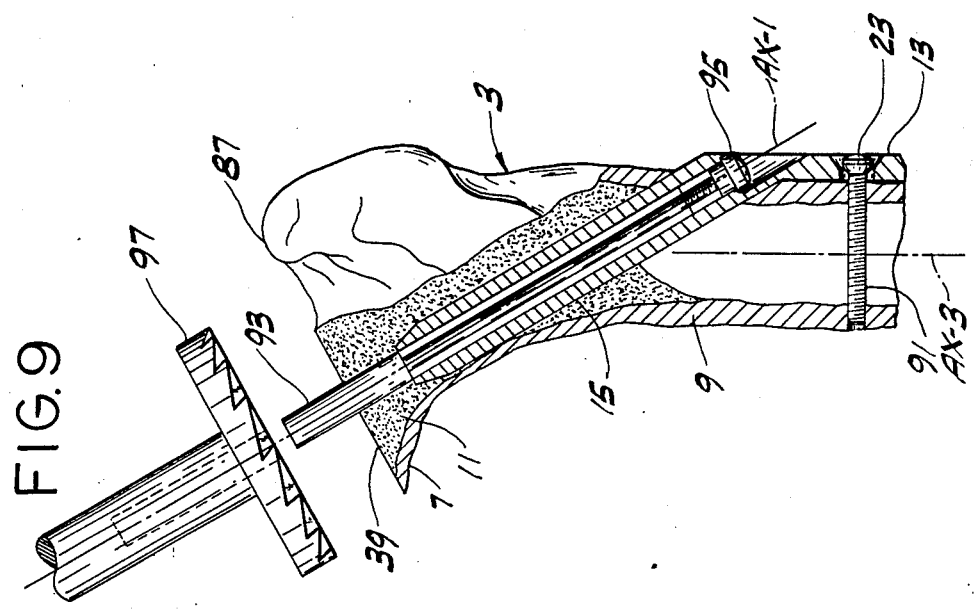
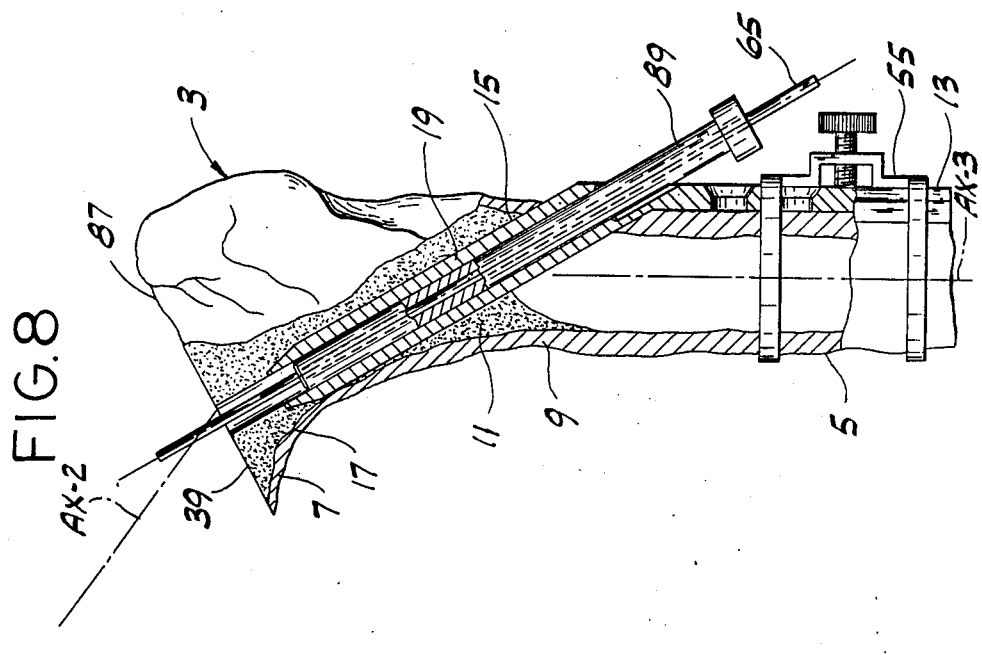

EXTRAMEDULLARY FEMORAL HEAD-NECK PROSTHESIS AND METHOD OF IMPLANTING SAME

BACKGROUND OF THE INVENTION

This invention relates generally to the art of femoral prosthetics, and more particularly to an improved femoral head-neck prosthesis and a method of implanting such a prosthesis.

Changes in the distribution of stress through a femur (thigh bone) after implanting a prosthesis may cause a number of complications, such as further deterioration of the bone. According to Wolff's law, changes in stress distribution through a bone eventually cause definite alterations in its internal structure. For example, if a portion of the femur is shielded from stresses that would normally occur, that portion is likely to deteriorate. On the other hand, where portions of the femur are subjected to greater stresses, those portions are likely to thicken in response. Of course, if the stresses are increased excessively bone cells will probably be killed ("necrosis").

Conventional "intramedullary" femoral head-neck implants, i.e., implants having a long stem secured in the medullary (marrow) canal of the femur, may cause deterioration of the femur since the proximal (upper) end of the femur is shielded from normal stress. As a result, an intramedullary prosthesis has a relatively short expected lifespan, at least relative to the expected lifespan of younger patients. Moreover, patients having intramedullary implants must reduce their activity substantially.

One approach to these problems is the "extramedullary" prosthetic joint disclosed in A. Huggler, U.S. Pat. No. 4,129,903. This prosthesis is also discussed in A. Huggler and H. Jacob, *The Uncemented Thrust-Plate Hip Prosthesis*, and A. Schreiber, H. Jacob, Y. Suezawa and A. Huggler, *First Results with the "Thrust Plate" Total Hip Prosthesis*, both in The Cementless Fixation of Hip Endoprosthesis 125–132 (E. Morscher ed. 1984) (hereinafter *Thrust-Plate Prosthesis* and *First Results*, respectively). The Huggler prosthesis includes a tension or tie rod through the bone, a pressure disc in contact with the femoral neck and a counter plate at the lateral side of the femur. One of the advantages of this kind of prosthesis is that there is sufficient supporting bone for an intramedullary implant if it becomes necessary to replace it.

There are, however, a number of undesirable side effects due to the Huggler prosthesis. For example, when the femur is loaded and unloaded as occurs during walking, the tension rod tends to move slightly with respect to the bone ("micromotion"), essentially because the modulus of elasticity of the bone and tie rod are different. As a result, the tie rod is almost constantly wearing at the bone and counter plate, possibly leading to fracture of the tie rod at its interface with the counter plate.

Huggler's approach includes positioning the thrust plate perpendicular to the longitudinal axis of the femoral neck and the tie rod along the longitudinal axis of the femoral neck (e.g., approximately 35 degrees from horizontal). According to Huggler, positioning the tie rod along the central longitudinal axis of the femoral neck is desirable to prevent motion of the tie rod relative to the bone and counter plate. More specifically, Huggler's position is that the more vertical the tie rod, the more the distal end of the tie rod will move within the counter plate (i.e., the greater the "micromotion").

However, since the tie rod of the Huggler prosthesis is aligned with the central longitudinal axis of the femoral neck, the tie rod is not aligned (or near alignment) with the generally vertical load on the femur caused by normal activity, such as walking. Thus, when the femur is loaded, the tie rod is subjected to a bending moment, which may lead to its fracture. This may have been a contributing cause to the tie rod fracture discussed in *Thrust-Plate Prosthesis*, at p. 127.

In addition, the Huggler prosthesis is anchored relatively high (proximal) on the lateral side of the femoral shaft where the cortical bone is relatively thin. This may be the reason that one-third of the patients treated with the prosthesis complained of pain in the first 6–8 months (*Final Results*, at p. 130), the pain apparently abating when the cortical bone has thickened sufficiently according to Wolff's law. Another cause of this pain may be the combination of the high position of the counter plate with its relatively high profile, which may cause irritation of muscles and tendons.

SUMMARY OF THE INVENTION

Among the several objects of the invention may be noted the provision of a femoral head-neck prosthesis which loads the femur in a manner similar to the original femoral head and neck thereby minimizing deterioration of the femur; the provision of such a prosthesis which protects the femur from movement of a replacement ball and ball stem relative to the femur as the femur is loaded and unloaded; the provision of such a prosthesis which allows a more normal lifestyle for a person in which it is installed; the provision of such a prosthesis which reduces the pain suffered by a person in which it is installed; and the provision of such a prosthesis that is durable, economical and long-lasting.

Additional objects which may be noted include the provision of a method of installing such a prosthesis which reduces complications and mistakes during installation; the provision of such a method which facilitates the proper alignment of the prosthesis; the provision of such a method which causes a minimum of trauma to a patient; the provision of such a method which allows installation with only a minimum of trial-and-error; and the provision of such a method which reduces the chances of undue heat build-up caused by friction, especially while cutting and drilling the femur, since excessive heat can kill bone cells.

Generally, an extramedullary femoral head-neck prosthesis of the present invention is implanted in a femur. The femur has a shaft and a neck at the upper end of the shaft at the medial side of the femur. The prosthesis comprises a sideplate and means for securing the sideplate to the femur shaft at the lateral side of the femur. A barrel extends obliquely upwardly from the sideplate and has an open upper end. The barrel is adapted to be inserted in a bore extending obliquely upwardly through the shaft of the femur from the lateral side of the shaft to the neck of femur. The prosthesis includes a ball assembly comprising a ball stem adapted to be inserted coaxially into the barrel through the open upper end of the barrel and to be slideably received therein. The ball stem is sized for a relatively close clearance fit in the barrel. A neck is provided at the upper end of the stem, and is adapted for face-to-face engagement with the neck of the femur. A ball is mounted on the neck. Retainer means is provided for holding the ball stem against upward movement of the stem in the barrel.

In general, a method of this invention involves implanting the extramedullary femoral head-neck prosthesis in the femur, the latter having a shaft and a neck at the upper end of the shaft at the medial side of the femur. The method includes cutting the neck of the femur to form a generally planar surface, and drilling a bore through the shaft of the femur to extend obliquely from the neck of the femur down to the lateral side of the shaft at an angle of approximately 30° with respect to the central longitudinal axis of the femur shaft. A barrel having an open end is inserted into the bore with the open end of the barrel facing upwardly and secured in fixed position in the bore. A stem of a ball assembly is inserted coaxially into the barrel to bring a generally planar surface of the ball assembly into face-to-face engagement with the planar surface of the femur neck.

Other objects and features will be in part apparent and in part pointed out hereinafter.

BRIEF DESCRIPTION OF THE DRAWINGS

FIG. 1 is a vertical cross-sectional view through a femoral head-neck prosthesis of the present invention as installed on a femur;

FIG. 2 is a partial side elevation of the prosthesis of FIG. 1 showing a sideplate for securing the prosthesis to the femur;

FIG. 3 is a view similar to FIG. 2, showing a sideplate of another embodiment of a femoral head-neck prosthesis of the present invention;

FIG. 4 is a side view of a device used in the method of the present invention holding a saw guide for cutting of the femoral neck;

FIG. 5 is a cross-sectional view along line 5—5 of FIG. 4

FIG. 6 is a side view of the device of FIG. 4 holding other accessories used in the method of the present invention;

FIG. 7 is a side view of the holding device of FIGS. 4-6 showing the femur being reamed;

FIG. 8 is a side view of the sideplate and barrel of the prosthesis of FIG. 1 being positioned on the femur; and FIG. 9 is a front elevation of a femur being planed according to the method of the present invention.

Corresponding reference characters indicate corresponding parts throughout the several views of the drawings.

DESCRIPTION OF PREFERRED EMBODIMENTS

Now referring to the drawings, an extramedullary femoral head-neck prosthesis of the present invention is designated in its entirety by the reference numeral 1. The femoral head-neck prosthesis is designed for implantation in a femur generally designated 3 having a shaft 5 and a neck 7 at the upper end of the shaft at the medial side of the femur. The femur includes hard layer of cortical bone 9 adjacent the surface of the bone and relatively soft cancerous bone 11 inside the femur.

As shown in FIG. 1, the prosthesis 1 generally comprises a sideplate in the form of an elongate member 13 and a barrel 15 integral with, and extending obliquely upwardly from, the sideplate. The barrel 15 has an open upper end 17, which is inserted in a bore 19 extending obliquely upwardly through the shaft 5 of the femur from the lateral side 21 of the shaft to the neck 7 of the femur.

The central longitudinal axis AX-,1 of the barrel 15 preferably extends at an angle A1 (FIG. 1) of approximately 150° with respect to the central longitudinal axis AX-5 of the sideplate 13. In addition, the longitudinal axis AX-2 of th femoral neck 7 and the longitudinal axis AX-1 of bore 19 and barrel 15 lie substantially in the same vertical plane P-1 (FIG. 5) as the central longitudinal axis AX-3 of the femoral shaft so that the load on the femur is as near "normal"(i.e., before implanting the prosthesis) as possible.

As shown in FIG. 2, means is provided for securing the sideplate 13 to the femoral shaft 5 so that the sideplate extends along the shaft at the lateral side 21 of the femur. For example, self-tapping screws 23 through a lower portion 24 of the side plate 13 may secure the sideplate to the thick cortical bone of the femoral shaft.

The prosthesis includes a ball assembly 25 comprising a ball stem 27 adapted to be inserted coaxially into the barrel 15 through the open upper end 17 of the barrel. The ball stem 27 has a flat surface 28 for engaging a corresponding flat portion (not shown)of barrel 15 to prevent rotation of the stem within the barrel. The stem 27 is sized for a relatively close clearance fit in the barrel, the stem being slideably received in the barrel. A at the upper end of the stem 27 engages the neck 7 of the femur face-to-face, covering the entire cut surface of the femoral neck 7 so that concentration of stress on only a portion of the neck is avoided. A ball 33 is removably attached to a neck 29 on the collar 31, the ball size being selected according to the length of the femoral neck and head indicated at 7 and 35, respectively (the femoral head being shown in FIG. 4).

Preferably, the central longitudinal axis (i.e., AX-1) of the stem 27 of the ball assembly 25 is skewed at an angle A2 (FIG. 1) of about 25° with respect to the central longitudinal axis AX-4 of the neck 29 of the ball assembly so that the center C of the ball is offset medially (to the left as viewed in FIG. 1) from the longitudinal axis AX-1 of the stem. When the ball stem 27 is inserted the barrel 15, the central longitudinal axis AX-4 of the ball neck 29 extends at about a 125° angle with respect to the central longitudinal axis AX-5 of the sideplate 13, the ball neck thus being approximately colinear with the axis AX-2 of the femoral neck 7.

The collar 31 of the ball assembly 25 has a downwardly-facing generally planar surface 37 extending generally at right angles to the central longitudinal axis AX-1 of the ball stem 27. The surface 37 is adapted for face-to-face engagement with a mating surface 39 on the femoral neck 7 by, for example, having metal beads on the surface or being "porous coated" to allow tissue ingrowth into the interstices of surface 37.

It will be observed that, since weight is carried generally along the barrel-stem axis AX-1, which is perpendicular to the planar surface 37, the load is carried by surface 37. This results in the bone being loaded by the prosthesis 1 substantially as it was by the natural femoral neck. In addition, the ball neck 29 will not tend to slide on the femoral neck 7 since the ball neck/femoral neck interface is approximately perpendicular to the load on the femur. In addition, an excessive bending moment on the stem 27 is avoided since the barrel-stem axis AX-1 of the prosthesis and the load on the femur are approximately aligned.

Retainer means is provided for holding the ball stem 27 against upward movement of the stem in the barrel 15 and for pulling the ball neck 29 against the femoral neck 7 to compress or preload the femoral neck. For example, the retainer means may include a set screw 41 threadable into the lower end 43 of the ball stem 27 when the latter is inserted in the barrel 15. The head of the set screw 41 is engageable with the lower end of the barrel 15 for holding the ball stem 27 against upward movement in the barrel.

It will be observed that the set screw 41 merely holds the stem in the barrel and compresses the femoral neck; it does not bear the weight of the patient. The femur 3, including the femoral neck 7, bears the weight of the patient in a near-normal fashion so that atrophy of the bone is prevented.

Moreover, since the ball stem 27 is slideably received in the barrel 15, friction or wear caused by motion of the stem relative to the barrel or bone would be between the stem and barrel. The bone is thus protected by the barrel 15. It will, therefore, be observed that "micromotion" and resulting wear on the femur are reduced or eliminated by this unique barrel-stem design.

FIG. 3 illustrates another embodiment of the invention generally corresponding to the embodiment of FIGS. 1 and 2, the principal difference being that the sideplate, here designated 13A, has an upper portion 45 above th juncture of the barrel 15A and the side plate in addition to a lower portion 24A below the juncture of the barrel and the sideplate. The upper and lower portions 45 and 24A, respectively, of the sideplate 13A have holes 47 therethrough for receiving fasteners (e.g., self-tapping screws 49) to secure the sideplate to the femur shaft 5.

While a number of different devices may be helpful for implanting the femoral head-neck prosthesis, a special device generally designated 51 and shown in FIGS. 4–7 is particularly adapted to be removably secured to the femoral shaft for holding a plurality of cutting, drilling and reaming accessories in position with respect to the femur.

As shown in FIG. 4, the holding device 51 comprises a body 53 adapted to be removably secured (e.g., by clamp 55) in face-to-face engagement with the femoral shaft 5, and an arm or outrigger portion 57 extending at an angle upwardly and outwardly from the body (e.g., at an angle of approximately 150 degrees with respect to the body) at one side of the femoral shaft 5. The upper end 59 of the arm is adapted to be centered with respect to the base of the femoral neck 7. When secured in the position shown, the arm 57 is at an angle of approximately 150 degrees with respect to the central longitudinal axis AX-3 of the femoral shaft 5.

As shown in FIG. 6, the body 53 of the holding device 51 includes a tubular guide member 61 having a bore therethrough for a starter drill (not shown). The tubular guide member 61 is adapted to be at an angle of approximately 90 degrees with respect to the central longitudinal axis AX-3 of the femur shaft 7 when the holding device is clamped thereto.

Preferably, holding device 51 includes a guide sleeve 63 for guiding a drill-tipped guide pin 65 into the femoral shaft 5 at an angle of approximately 30 degrees with respect to the central longitudinal axis AX-3 of the shaft. The sleeve 63 is preferably adapted to be slideably received in a guide barrel 67 formed as an integral part of the body 53 of device 51. The sleeve 63 is separately removable from the guide barrel 67 so that after the guide pin 65 has passed through the femoral neck 7, the sleeve may be removed while the guide pin remains in position.

As noted above, device 51 is adapted for holding a variety of different accessories used in implanting the prosthesis 1 of the present invention. One such accessory is a saw guide 69 adapted to be detachably mounted at the upper end 59 of the arm 57 for guiding a saw blade to cut the femoral neck 7 to form surface 39. As shown in FIG. 4, the saw guide 69 has a sawcut slot 71 generally perpendicular to the central longitudinal axis of arm 57, the arrangement being such that when the holding device 51 is secured in the position shown, the slot is at an angle of approximately 60 degrees with respect to the central longitudinal axis AX-3 of the femoral shaft 5. It is contemplated that the slot 71 will also be generally perpendicular to the central longitudinal axis of the arm 57. The saw guide 69 is slideably adjustable along the arm 57 to properly position it with respect to the femoral neck 7. A set screw 73 is provided for securing the saw guide in adjusted position.

Indicated generally at 75 is another accessory for checking the position of the holding device 51 with respect to the femur 3. Accessory 75 is slideably adjustable along arm 57 to properly position it with respect to surface 39 of the femoral neck. The accessory i not rotatable with respect to the arm 57. A set screw 79 is provided for detachably securing the accessory 75 in adjusted position. Accessory 75 comprises a relatively thin flat member 80 extending laterally outwardly to a position in which it is disposed in a plane generally parallel to and immediately above surface 39. Member 80 has an opening 81 in alignment with the central longitudinal axis of the guide sleeve 63. Thus, opening 81 is adapted for indicating the location on the cut surface 39 of the femoral neck where the guide pin will come through so that the position of the holding device 51 may be checked for accuracy prior to drilling. It will be noted that arm 57 of the holding device 51 is preferably parallel to the central longitudinal axis of the guide sleeve and barrel 63 and 67, respectively, so that the sleeve and barrel axis is aligned with the opening 81 regardless of the position of the accessory 75 along the arm.

A cannular reamer 83 (FIG. 7) is sized to be slideably received in the barrel 67. A central axial bore 84 through the reamer 83 is sized to slideably receive the guide pin 65 therein. It will be observed that the reamer 83 is adapted to slide into the guide barrel 67 over the guide pin 65 so that the guide pin and barrel guide the reamer as it reams the bore 85 created by the guide pin. The reamer 83 may rotate around a stationary guide pin 65, or the reamer and the guide pin may rotate together. It will be observed that during the reaming process, the guide pin 65 projects through the opening 81 in member 80. This serves to stabilize the guide pin 65 while the femur is being reamed.

To install the prosthesis 1 in the femur in accordance with the method of this invention, the hip joint and the lateral (i.e., right in the drawings) side of the femur are first surgically exposed. A vertical plane P-1 through the central longitudinal axis AX-2 of the femoral neck 7 is typically at an angle of approximately 15 degrees anterior to a lateral-medial plane P-2 through the central longitudinal axis AX-3 of the femoral shaft 5, as shown in FIG. 5. This angle is commonly referred to as the "anteversion" of the femoral neck 7. Accordingly, the device 51 is positioned radially on the femur such that the vertical axis of body 53 lies in plane P-1 approximately 15 degrees posterior from the lateral-medial plane P-2 (since the body is lateral of axis AX-3 and the femoral neck 7 is medial). In this position, a vertical plane P-3 through arm 57 should be parallel to plane P-1. In addition, the holding device 51 is positioned proximally-distally on the femur such that the upper end 59 of arm 57 is centered with respect to the base of the femoral neck 7, as shown in FIG. 4. The device 51 is then clamped on the femoral shaft 5 by clamp 55.

The saw guide 69 is positioned (proximally-distally) on arm 57 such that the slot 71 is located adjacent the base of the femoral neck 7 and generally aligned with the upper surface of the lateral femoral cortex 87 of the femur, as shown in FIG. 4. In this position, the slot 71 should be at an angle of approximately 60 degrees with respect to the central longitudinal axis AX-3 of the femoral shaft 5. Then set screw 73 is tightened to firmly attach the saw guide 69 to the arm 57.

With the saw guide 69 in place, the neck 7 is cut with an oscillating saw (not shown) by passing the saw through the slot 71 to form surface 39 extending from the lateral femoral cortex 87 at an angle of approximately 60 degrees with respect to the central longitudinal axis AX-3 of the femoral shaft 5. The saw guide 69 is then removed from the arm 57, leaving the device 51 attached to the femoral shaft in its original position, and the femoral head 35 is removed.

If a total hip replacement (i.e., replacement of the femoral head 35 and acetabulum (not shown)) is required, the acetabulum should now be prepared.

As shown in FIGS. 6 and 7, the opening 81 in member 80 of assessory 75 is centered with respect to the surface 39 and secured to the arm 57. Some adjustment of the holding device 51 may be necessary to center opening 81 with respect to the surface 39 of the femoral neck. This may be accomplished by loosening the clamp 55 and adjusting the body 57 of the device 51. For example, if opening 81 is too medial (i.e., leftward in the drawings), the holding device 51 should be positioned more proximal on the femoral shaft 5 (upward in the drawings), and if the opening is too lateral (rightward in the drawings), the pin should be positioned more distal on the femoral shaft. In addition, if the opening 81 is anterior or posterior to the center of surface 39, the "antevession" may be adjusted by slightly turning the device 51 on the femoral shaft 5.

With the opening 81 centered, a drill (not shown) is inserted through the tubular guide member 61 to make a relatively short starter hole (also not shown) in the lateral femoral cortex.. Without a starter hole, the guide pin 65 might tend to travel or "walk" along the lateral femoral cortex due to the acute angle of entry, or be deflected from it correct angle (e.g., 30 degrees) through the femur. The guide sleeve 63 should now be inserted in the guide barrel 67 of the holding device 51.

The drill-tipped guide pin 65 is then inserted into the guide barrel 67, and a bore 85 is drilled up through the lateral femoral cortex and through the cut surface 39 of the femoral neck 7. The bore 85 extends obliquely from the neck 7 of the femur down to the lateral side of the shaft at an angle of approximately 30° with respect to the central longitudinal axis of the femur shaft. The guide pin 65 should exit the cut surface 77 of the femoral neck 7 through the opening 81 of accessory 75.

If the guide pin 65 is significantly (e.g., more than 5mm) off center, the holding device 51 should be adjusted. For example, if the pin 65 is too medial (i.e., leftward in the drawings), the device 51 should be positioned more proximal on the femoral shaft 5 (upward in the drawings), and if tee pin is too lateral (rightward in the drawings), the pin should be positioned more distal on the femoral shaft. In addition, if the pin 65 extends through surface 39 anterior or posterior of the opening 73, the "anteversion" may be adjusted by slightly turning the device 51 on the femoral shaft 5. It should, however, be noted that device 51 will reduce or eliminate the trial-and-error process discussed in this paragraph.

When the guide pin 65 is in the right position, the guide sleeve 63 is removed from the guide barrel, and the guide pin and accessory 75 are left in place. As noted above, accessory 75 stabilizes the proximal end of the guide pin 65.

As shown in FIG. 7, the cannular reamer 83 is then inserted in the guide barrel 67 over the guide pin 65 to form bore 19 through the lateral femoral cortex at an angle of approximately 30 degrees with respect to the central longitudinal axis AX-3 of the femoral shaft 5. Since the body 53 of the holding device is ante-verted approximately 15 degrees with respect to the femur, the bore 19 lies in plane P-1 (and is approximately 15 degrees anteriorly oriented with respect to the transverse axis of the knee, which is parallel to lateral-medial plane P-2). The holding device 51 is then removed from the femur.

In the next step of the process, the barrel 15 of the prosthesis 1 is inserted into the bore 19 with the open end 17 of the barrel facing upwardly. A pin sleeve 89 (FIG. 8) is inserted into the barrel 15, and the guide pin 65 is inserted into the sleeve to recheck the position of the bore 19 with respect to the center of surface 39 of the femoral neck. The radial orientation or "anteversion" of bore 19 is also checked. The longitudinal axis AX-2 of the femoral neck 7 and the axis AX-1 of bore 19 should lie in the same vertical plane P-1 as the central longitudinal axis AX-3 of the femoral shaft. This plane is at an angle of approximately 15 degrees with respect to the transverse axis (not shown) of the knees, which is parallel to plane P-2.

If the position of the prosthesis 1 is satisfactory, the sideplate 13 is clamped in place, and the pin sleeve 89 and guide pin 65 are removed. Holes 91 are then drilled through the screw holes in the sideplate 13, and self-tapping screws 23 of appropriate length are inserted through the sideplate to fasten it to the femoral shaft 5, thereby securing the barrel 15 in fixed position in the bore 19.

After the sideplate 13 and barrel 15 are secured to the femur, a planing trunnion 93 is inserted into and suitably secured to the barrel against rotational and axial movement relative to the barrel so that it projects upwardly from the surface 39 of the femoral neck, as shown in FIG. 9. For example, the trunnion 93 may be secured against rotational movement by corresponding flat surfaces inside the prosthesis barrel 15 and on the trunnion, and against axial movement by a set screw 95. A femoral neck planer 97 is then placed on the trunnion 93, and surface 39 of the femoral neck 7 is planed perpendicular to the axis of the barrel while even pressure is applied to the planer. After planing, the planer 97 and trunnion 93 are removed.

A trial neck-collar-stem assembly (similar to ball assembly 25) is then inserted into the femoral neck and the barrel 15. The collar of this assembly (similar to collar 31) is pulled against surface 39 of the femoral neck by tightening a set screw (similar to set screw 41).

The undersurface of the collar includes a pressure sensor indicator (e.g., pressure sensitive paper) so that the evenness of the load may be determined. If there is an uneven distribution of load on surface 39 of the femoral neck 7, the planer 97 may be used to plane down the high portions causing the uneven distribution.

Once the femoral neck 7 is satisfactorily planed, the stem 27 of an appropriate size ball assembly 25 is inserted through the femoral neck coaxially into the barrel 15 to bring generally planar surface 37 of the ball assembly into face-to-face engagement with the planar mating surface 39 of the femur neck. Set screw 41 is inserted through the sideplate 13 into barrel 15, and tightened with a screw driver (not shown) having a torque gauge. The set screw 41 is tightened to compress the femoral neck 7 sufficiently to limit "micromotion" between the prosthesis 1 and the femur 3. Overtightening should be avoided, as bone necrosis (death) may be caused by excessive compression.

The ball 33 of the prosthesis 11 is then placed in the acetabulum (not shown), and the surgically formed opening is closed.

It will be observed from the foregoing that the prosthesis is properly positioned with respect to the femur with a minimum of trial-and-error, and the femur is loaded in a near "normal" way by the prosthesis, thereby reducing the patient's pain and preventing deterioration of the femur after implantation the prosthesis.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. An extramedullary femoral head-neck prosthesis for implantation in a femur having a shaft and a neck at the medial side of the femur, comprising:
   a sideplate;
   means for securing the sideplate to the femur shaft at the lateral side of the femur;
   a barrel extending obliquely upwardly from the sideplate and having an open upper end, said barrel being adapted to be inserted in a bore extending obliquely upwardly through the shaft of the femur from the lateral side of the shaft to the neck of the femur;
   a ball assembly comprising a ball stem having a central longitudinal axis adapted to be inserted coaxially into the barrel through the open upper end of the barrel and to be slideably received therein, said ball stem being sized for a relatively closed clearance fit in said barrel, a collar at one end of the stem, constituting its upper end, adapted for face-to-face engagement with the neck of the femur, a neck on the collar, and a ball on the neck, said neck having a central longitudinal axis which is skewed relative to the central longitudinal axis of the stem so that the center of the ball is offset medially from the longitudinal axis of the stem; and
   retainer means for holding the ball stem against upward movement of the stem in the barrel.

2. An extramedullary femoral head-neck prosthesis as set forth in claim 1 wherein said sideplate is an elongate member having a central longitudinal axis and is adapted to extend along the femur shaft.

3. An extramedullary femoral head-neck prosthesis as set forth in claim 2 wherein the central longitudinal axis of the barrel extends at an angle of approximately 150° with respect to the central longitudinal axis of the sideplate.

4. An extramedullary femoral head-neck prosthesis as set forth in claim 3 wherein when the ball stem is inserted in said barrel, the central longitudinal axis of the neck is skewed at an angle of about 25° to the central longitudinal axis of the stem.

5. An extramedullary femoral head-neck prosthesis as set forth in claim 1 wherein said sideplate and barrel are integrally formed.

6. An extramedullary femoral head-neck prosthesis as set forth in claim 1 wherein said retainer means comprises a set screw threadable into the lower end of the ball stem when the latter is inserted in the barrel, said set screw being engageable with the barrel for holding the ball stem against any substantial upward movement of the stem in the barrel.

7. An extramedullary femoral head-neck prosthesis as set forth in claim 1 wherein the central longitudinal axis of the neck is skewed at an angle of about 25° relative to the central longitudinal axis of the stem.

8. An extramedullary femoral head-neck prosthesis as set forth in claim 1 wherein said sideplate has an upper portion above the junction of the barrel and the sideplate, and a lower portion below the junction of the barrel and the sideplate.

9. An extramedullary femoral head-neck prosthesis as set forth in claim 1 wherein said collar has a downwardly-facing generally planar surface extending generally at right angles to the central longitudinal axis of the stem, said surface being adapted for face-to-face engagement with an upwardly-facing mating surface on the neck of the femur.

* * * * *